United States Patent
Ku

(10) Patent No.: US 7,542,131 B2
(45) Date of Patent: Jun. 2, 2009

(54) APPARATUS FOR MEASURING BLOOD CELL DEFORMABILITY

(75) Inventor: Yun-Hee Ku, Gyeongsangbuk-Do (KR)

(73) Assignee: Sewon Meditech, Inc., Buk-gu, Daegu (KR)

( * ) Notice: Subject to any disclaimer, the term of this patent is extended or adjusted under 35 U.S.C. 154(b) by 157 days.

(21) Appl. No.: 10/559,407

(22) PCT Filed: Jun. 22, 2004

(86) PCT No.: PCT/KR2004/001493

§ 371 (c)(1),
(2), (4) Date: Dec. 5, 2005

(87) PCT Pub. No.: WO2004/113908

PCT Pub. Date: Dec. 29, 2004

(65) Prior Publication Data

US 2006/0119836 A1 Jun. 8, 2006

(30) Foreign Application Priority Data

Jun. 23, 2003 (KR) .................... 10-2003-0040650
Jun. 8, 2004 (KR) .................... 10-2004-0041673

(51) Int. Cl.
*G01N 33/48* (2006.01)
(52) U.S. Cl. ....................................... 356/39
(58) Field of Classification Search ....... None
See application file for complete search history.

(56) References Cited

U.S. PATENT DOCUMENTS

| | | | | |
|---|---|---|---|---|
| 3,955,890 A | * | 5/1976 | Bessis et al. | 356/39 |
| 4,428,669 A | * | 1/1984 | Bessis | 356/39 |
| 4,435,080 A | * | 3/1984 | Maly et al. | 356/426 |
| 5,327,777 A | * | 7/1994 | Kaye et al. | 73/54.06 |
| 6,193,667 B1 | * | 2/2001 | Kensey | 600/573 |
| 6,322,525 B1 | * | 11/2001 | Kensey et al. | 600/573 |
| 6,422,065 B1 | * | 7/2002 | Shine et al. | 73/53.01 |
| 6,540,895 B1 | * | 4/2003 | Spence et al. | 204/450 |
| 2007/0119714 A1 | * | 5/2007 | Schnelle et al. | 204/547 |

FOREIGN PATENT DOCUMENTS

JP 08122328 A * 5/1996

* cited by examiner

*Primary Examiner*—Gregory J Toatley, Jr.
*Assistant Examiner*—Gordon J Stock, Jr.
(74) *Attorney, Agent, or Firm*—G W i P S

(57) ABSTRACT

A disposable blood test kit inserted into an instrument for measuring the blood cell deformability is provided to avoid a washing process during a blood test. The instrument comprises a disposable blood test kit (20) for directly containing the blood sample, a light emitting unit (10) disposed above the disposable blood test kit (20), and a measurement unit (30) for measuring the blood cell deformability. The disposable blood test kit (20) comprises a blood sample pot (21) for containing the blood sample, a slit channel (22) made of a transparent material, and a tiny waste blood pot (23) for collecting the tested blood sample. A differential pressure is applied to the disposable blood test kit (20) to make the stagnant blood sample flow through the slit channel (22) and to collect the tested blood sample at the tiny waste blood pot (23).

10 Claims, 10 Drawing Sheets

APPARATUS FOR MEASURING BLOOD CELL DEFORMABILITY

BACKGROUND OF THE INVENTION

1. Field of the invention

The present invention relates to an instrument for measuring blood cell deformability. More particularly, a disposable blood test kit is provided to avoid a washing process during a blood test.

2. Related prior art

As the blood cell deformability is recently known to affect the viscosity and various characteristic of the blood cell directly, research is actively attempted to develop the measuring device for the blood cell deformability.

Especially, a journal entitled Clinical Hemorheology and Microcirculation (Vol. 14, pp. 605-618, 1994) introduces a Laser-Assisted Optical Rotational Cell Analyzer (LORCA) formed as a concentric dual tube of a rotary Couette flow system for measuring the blood cell deformability. This device emits a laser beam to the blood cell during rotation and captures the diffracted image by a CCD camera for analyzing by the computer programming and for measuring the blood cell deformability.

Because the shear force or shear rate applied to the blood cell varies according to the spinning speed, it is required repeatedly to measure the shear force or shear rate of the blood cell at the various ranges of the spinning speed.

The conventional device has a disadvantage in that the surface of the instrument contacted with the blood sample must be washed after the experiment.

Further, another journal entitled Blood Cells, Molecules and Diseases (Vol. 28, pp. 373-384) introduces a blood cell deforming distribution tester (ARCA). A diluted blood sample is injected between the spinning parallel disks of the ARCA to capture through a microscopic CCD camera the images that illustrate the blood cell deformation by the shearing forces due to the spinning speed. Then, the distribution of the blood cell deformation is obtained by the curve-fitting computer program through the analysis of the clearly captured images depending on the various shearing forces.

This conventional device also has as a disadvantage that it takes one to two hours to analyze the captured images of the blood samples, and the surface of the instrument contacted with the blood sample must be washed after the experiment.

On the other hand, a common problem of the conventional instruments is that the surface of the instrument contacted with the blood sample must be washed after each experiment. Thus, it is inconvenient and burdensome to maintain the sanitary instrument after washing.

Further, special training is required to operate such conventional instruments, and professional instruction is required to analyze the blood samples. Thus, such conventional instruments are not suitable for practical use in a clinical setting.

SUMMARY OF THE PRESENT INVENTION

In order to solve the aforementioned problem, an instrument of the present invention is provided for measuring the red blood cell deformability comprising a disposable blood test kit to get rid of the washing process after the blood test. The disposable kit requires a tiny amount of blood sample for testing. The testing time is also shortened for measuring the blood cell deformability compared with the conventional instruments.

An objective of the present invention is to provide an instrument for measuring blood cell deformability comprising a disposable blood test kit (20) for directly containing the blood sample, a light emitting unit (10) disposed above the disposable blood test kit (20), and a measurement unit (30) for measuring the blood cell deformability. The disposable blood test kit (20) comprises a tiny blood sample pot (21) for containing the blood sample, a slit channel (22) for flowing the blood sample by the pressure difference, and a tiny waste blood pot (23) for collecting the tested blood sample. The measurement unit (30) comprises: a differential pressure generator (33) connected to the disposable blood test kit (20) through a connecting tube and a valve (32) for generating the pressure difference between the tiny blood sample pot (21) and the tiny waste blood pot (23); a pressure gauge (34) connected to the differential pressure generator (33) and the disposable blood test kit (20) for measuring the pressure difference; a screen (31) for projecting the diffracted images of the blood cell; an image capturing unit (35) for capturing the diffracted images; a control unit (36) for calculating the blood cell deformability with variation of the shearing force, which are determined through a computer analyses on time based data of the captured images and the pressure measurements; an output unit (37) for printing the calculated information on the sheet or displaying on an LCD screen; and a memory unit (38) for storing the calculated information and images.

Another objective of the present invention is to provide the differential pressure generator (33) connected to the tiny waste blood pot (23) of the disposable blood test kit (20) through a connecting tube and a valve (32) for generating vacuum pressure at the tiny waste blood pot (23), so that the blood sample flows toward the tiny waste blood pot (23) through the slit channel (22).

The slit channel (22) is optically transparent and has a clearance with a rectangular shape. The disposable blood test kit (20) is made of a transparent material such as silicon, silica, quartz, glass, a polymer produced by a laser, an extruded polymer or ceramics.

Still another objective of the present invention is to provide the differential pressure generator (33) connected to the tiny blood sample pot (21) of the disposable blood test kit (20) through a connecting tube and a valve (32) for generating positive pressure at the tiny blood sample pot (21), so that the blood sample flows toward the tiny waste blood pot (23) through the slit channel (22). The image-capturing unit (35) enables capturing the diffracted image of the deformed blood cell by projecting on the screen. Alternatively, the image-capturing unit (35) enables directly capturing the diffracted image of the deformed blood cell without projecting on the screen. The image capturing unit (35) can be adopted a CCD sensor array, a CCD camera, a digital camera, a web camera, or a video camera for capturing the diffracted images. The light-emitting unit (10) is adopted either as a Laser Diode or Light Emitting Diode (LED).

Still another objective of the present invention is to provide a heat control device, such as a thermoelectric component, a temperature control block or a hot-cold water jacket, or a halogen-lamp, which is used for adjusting and maintaining constant testing temperature surrounding the disposable blood test kit.

THE DETAILED DESCRIPTION OF THE PREFFERED EMBOBIMENT

Figure 1:
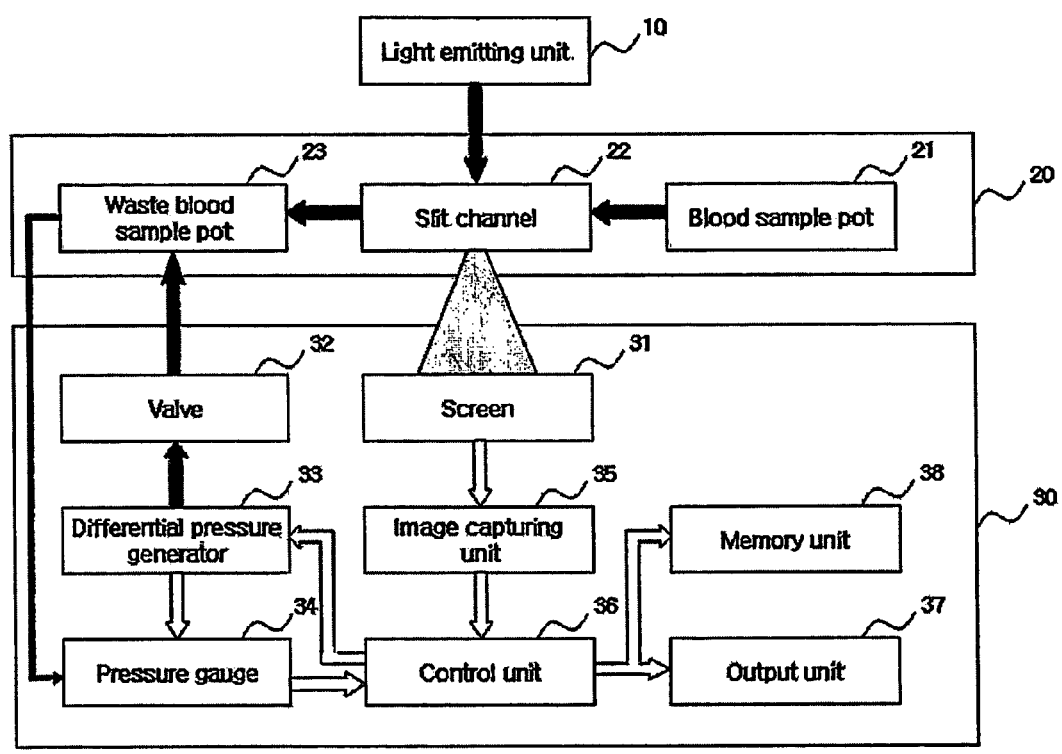
FIG. 1 is a configuration of an instrument equipped with a negative pressure generator for measuring the blood cell deformability according to the present invention.

In order to achieve the above-mentioned objectives, the present invention provides an instrument for measuring the blood cell deformability comprising a disposable blood test kit (20) directly containing the blood samples, a light emitting unit (10) disposed above the disposable blood test kit (20), and a measurement unit (30) for measuring the blood cell deformability. The disposable blood test kit (20) comprises a tiny blood sample pot (21) for injecting and containing the blood sample, a slit channel (22) for flowing the blood sample by the pressure difference, and a tiny waste blood pot (23) for collecting the tested blood sample. The base of the tiny blood sample pot (21) is connected to one end of the slit channel (22) for flowing the blood sample. The base of the tiny waste blood pot (23) is connected to the opposite end of the slit channel (22) for collecting the tested blood sample.

Between the tiny blood sample pot (21) and tiny waste blood pot (23), the pressure difference occurs due to atmospheric pressure, and the blood sample is flown through a tiny slit channel (22) on each probe of the disposable blood sample test kit (20).

The measurement unit (30) comprises: a differential pressure generator (33) which is connected to the disposable blood test kit (20) through a connecting tube and valve (32) for generating the different pressures between the tiny blood sample pot (21) and tiny waste blood pot (23), so that the blood sample passes through the slit channel of the disposable blood sample test kit (20); a pressure gauge (34) connected to the differential pressure generator (33) and the disposable blood sample test kit (20) for sequentially indicating the differential pressure; a screen (31) for projecting the diffracted images of the blood cells, which were generated by light diffracting of blood cells passing through the slit channel; an image capturing unit (35) for capturing the images; a control unit (36) for determining the blood cell deformability and the shearing force on time based data of the captured images and measured pressure through the computer image analysis; an output unit (37) for printing the calculated information on the sheet or displaying on an LCD screen; and a memory unit (38) for storing the calculated information and images.

The diluted blood sample is injected into the tiny blood sample pot (21) of the disposable blood test kit (20). When the blood sample penetrates through the slit channel and passes underneath the light emitting unit (10), the emitted light is diffracted through the deformed blood cell to project the images on the screen. The instrument of the present invention has equipped a Laser diffraction device and a driving pressure varying device to measure and analyze the blood cell deformability.

Hereinafter, the instrument of the present invention for measuring the red blood cell deformability is described accompanied by the detailed drawings.

As shown in FIG. 1, a configuration of the instrument for measuring the blood cell deformability of the present invention comprises a light emitting unit (10) for emitting the light to the blood sample, a disposable blood test kit (20) for containing the blood sample, and a measurement unit (30) for measuring the blood cell deformability.

The light-emitting unit (10) disposes above the disposable blood test kit for radiating the light to the blood sample.

The disposable blood test kit (20) comprises a tiny blood sample pot (21) for injecting and containing the blood sample, a slit channel (22) for flowing the blood sample by the pressure difference, and a tiny waste blood pot (23) for collecting the tested blood sample. The base of the tiny blood sample pot (21) is connected to one end of the slit channel (22) for flowing the blood sample. The base of the tiny waste blood pot (23) is connected to the opposite end of the slit channel (22) for collecting the tested blood sample.

The measurement unit (30) comprises: a differential pressure generator (33) connected to the disposable blood test kit (20) via a connecting tube and valve (32) to generate a vacuum pressure at the tiny waste blood pot (23) for driving the blood sample through the slit tunnel of the disposable blood sample test kit (20); a pressure gauge (34) connected to the differential pressure generator (33) and the disposable blood sample test kit (20) for continuously measuring the differential pressures; a screen (31) for projecting the diffracted images of the blood cells which are passed through the slit channel; an image capturing unit (35) for capturing the images; a control unit (36) for calculating the blood cell deformability with variation of the shearing force, which are determined on time based data of the captured images and the pressure measurements by the computer analyses; an output unit (37) for printing the calculated information on the sheet or displaying on an LCD screen; and a memory unit (38) for storing the calculated information and images.

At this point, the image capturing unit (35) enables capturing the deformed blood cell diffraction image projected on the screen while the blood sample is passed under the light emitting unit through the slit channel (22). For capturing the images, the image capturing unit (35) can be adopted either a CCD camera, digital camera, web camera, or a video camera. Alternatively, the deformed blood cell diffraction image can be directly captured by the image-capturing unit (35) without projecting on the screen by adopting a CCD sensor array as the image capturing unit (35). The CCD sensor array is able to detect the light intensity of the diffracted images and determine the blood cell deformation from the detected light signal on the sensor array. Thus, the deformability can be determined from the diffracted light, which is directly projected on the CCD-sensor array without projecting screen.

Figure 2:
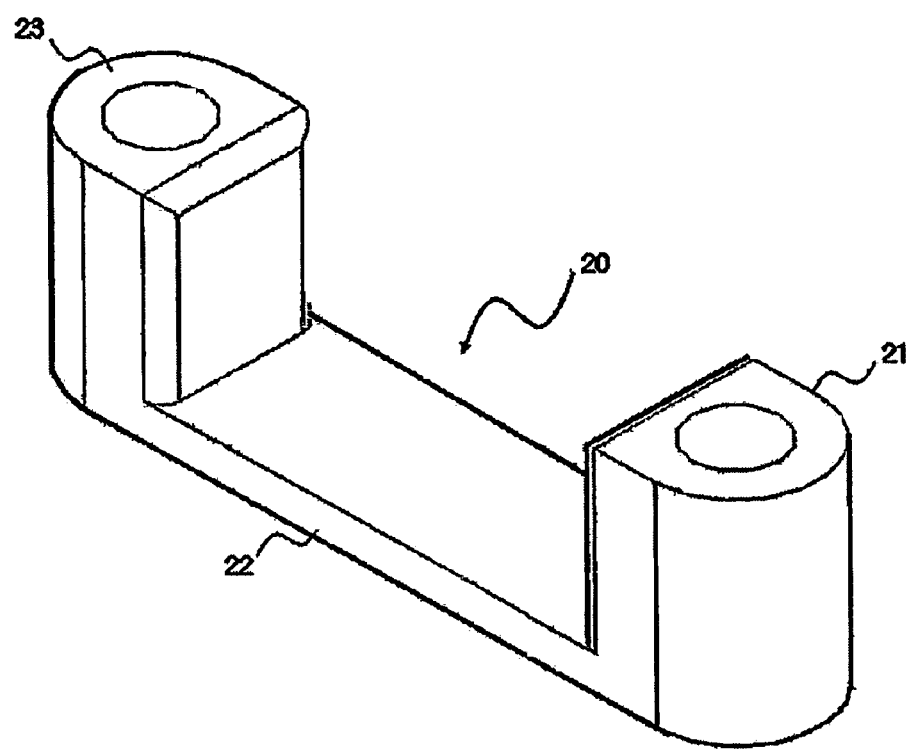
FIG. 2 is a disposable blood test kit inserted into the instrument for measuring the blood cell deformability according to the present invention.

As shown in FIG. 2, a disposable blood test kit, which is inserted into the instrument for measuring the blood cell deformability, is presented.

As discussed above, the disposable blood test kit (20) is integrally formed with a tiny blood sample pot (21), a slit channel (22) and a tiny waste blood pot (23). Especially, the clearance of the slit channel (22) is 200 micrometers in this invention. However, the clearance of the slit channel (22) could be manufactured to be ten to one hundred micrometers.

Also, a lid made of silicon or rubber is provided to close tightly either the tiny blood sample pot (21) or tiny waste blood pot (23).

For a blood test, the present disposable blood test kit (20) requires a very small amount of blood sample, i.e. five microliters of blood sample is needed for one blood test. The high viscosity liquid, such as a PVP in PBS solution, is used to dilute the blood sample for measuring the blood cell deformability.

Figure 3:
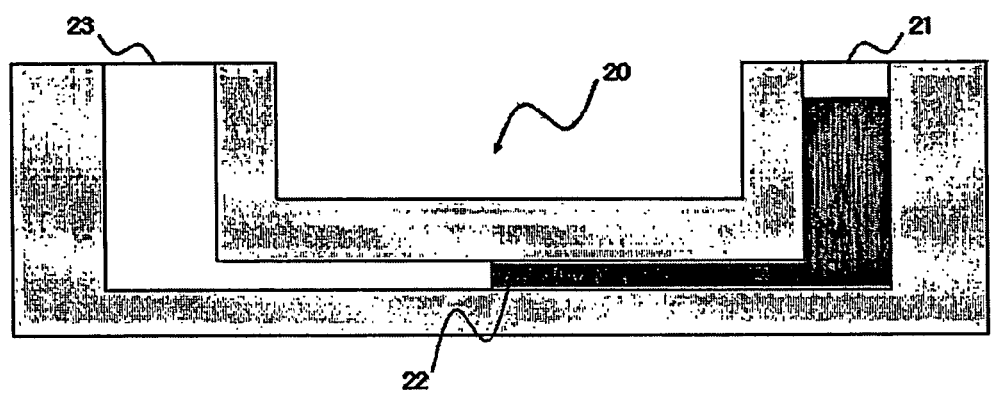
FIG. 3 illustrates an initial state of the blood sample dropped in the disposable blood test kit for measuring the blood cell deformability according to the present invention.

As seen in FIG. 3, an initial state is shown when the blood sample is dropped in the tiny blood sample pot (21) of the disposable blood test kit for measuring the blood cell deformability.

As the blood sample is dropped in the tiny blood sample pot (21), the blood sample is penetrated to the halfway point of the slit channel (22) due to the capillary effect. However, the blood sample won't advance beyond the halfway point of the slit channel (22) due to the thick viscosity.

At this point, a vacuum pressure is applied to the tiny waste blood pot (23) to suck out the stagnant blood sample from the halfway point of the slit channel (22) and to collect the tested blood sample at the tiny waste blood pot (23). Due to the vacuum pressure at the tiny waste blood pot (23), the stagnant blood sample in the slit channel (22) is exposed to a shear force with fluid resistance. Therefore, the stagnant blood sample in the slit channel (22) flows to the tiny waste blood pot (23).

Figure 4:
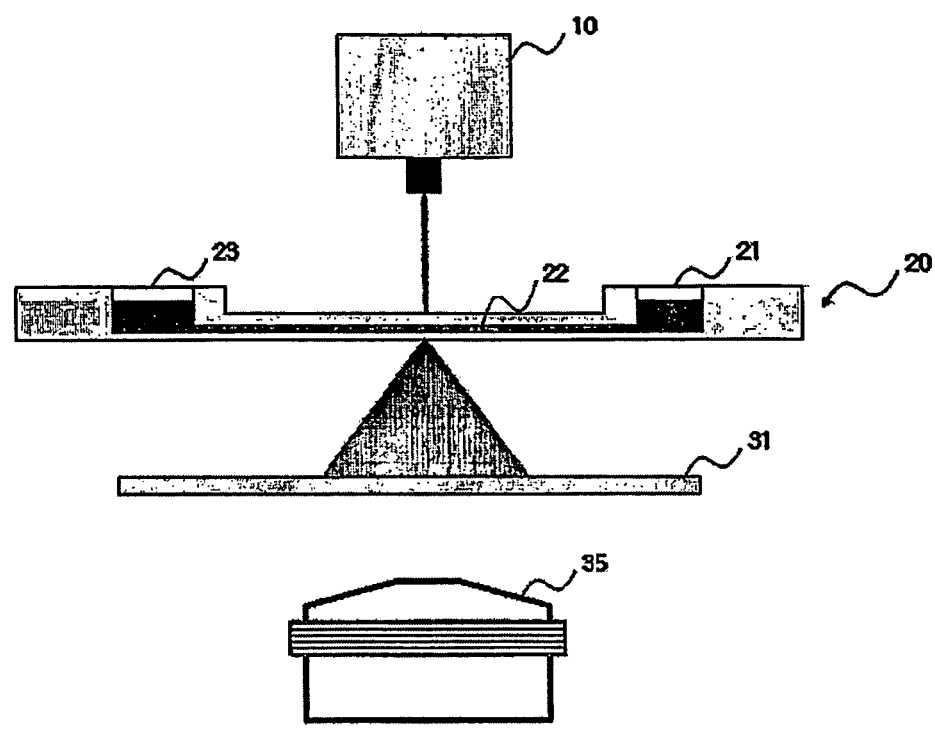
FIG. 4 is an overall outer configuration of the instrument for measuring the blood cell deformability according to the present invention.

Referring to FIG. 4, an operating manual of the instrument for measuring the blood cell deformability is presented as follows:

The light-emitting unit (10) consisting of a Laser Diode or Light Emitting Diode (LED) is located above the disposable blood test kit (20) for illuminating the light beam to the blood sample. The slit channel (22) is made of a transparent material to transmit the light beam. The illuminated beam is diffracted on the deformed blood cell and projected on the screen. The image-capturing unit (35) enables capturing the deformed blood cell diffraction image, which is projected on the screen. At this point, the deformed blood cell diffraction image can be directly captured by the image-capturing unit (35) such as a CCD-sensor array without projecting on the screen.

Figure 5:
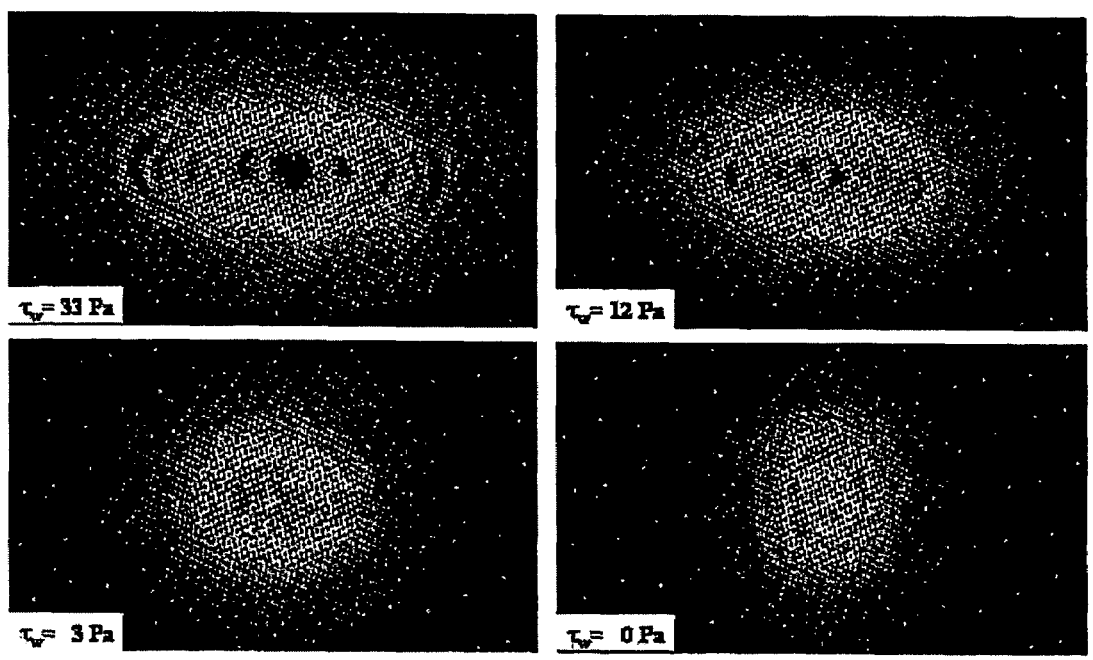
FIG. 5 illustrates the various laser diffraction images of the deformed red blood cell images, which are captured through the instrument for measuring the blood cell deformability according to the present invention.

As shown in FIG. 5, an example of the various diffraction images captured through the present instrument for measuring the blood cell deformability is presented. As seen in the picture, the red blood cell has a circular shape at near zero shear force. However the red blood cell is deformed to an ellipse shape at the high shear force.

When a plurality of blood cells flows through the slit channel (22), the blood cells are influenced by the shear forces. At this point, the light beam with proper wavelength is radiated to the deformed blood cells, and the light beam will be diffracted through the deformed blood cells and projected on the screen as an integrated image.

The deformation of the blood cell varies depending on the magnitude of the speed of the moving blood and on the activating shearing force. Especially, the speed of the moving blood sample is faster at the initial stage due to the high initial vacuum pressure. Since the strong shear force is activated to the blood cell at the beginning of the test, the blood cell will be deformed larger, generating a large ellipse shape of the deformed blood cell. Therefore, the deformed blood cell image has a large ratio of length to breadth.

Contrary, since the speed of the moving blood sample is gradually decreased as the test progresses, the blood cell has a tendency to restore the original shape. Therefore, the diffracted blood cell image is restored back to the circular shape due to the decreasing of the shear force.

On the other hand, the image capturing unit (35) captures the deformed blood cell image for analyzing the deformability of the blood cell in the ratio of length and breadth and for determining the Deformation Index (DI) through the image analysis computer programming. The images of the blood cell diffraction captured by the image-capturing unit (35) are analyzed by ellipse curve-fitting computer software to determine the length (L) and width (W) of the analyzed elliptic images, and calculating the Deformation Index (DI). The Deformation Index "$DI = (L-W)/(L+W)$" is defined as the ratio of the difference to the sum of the length and the width.

Figure 6:
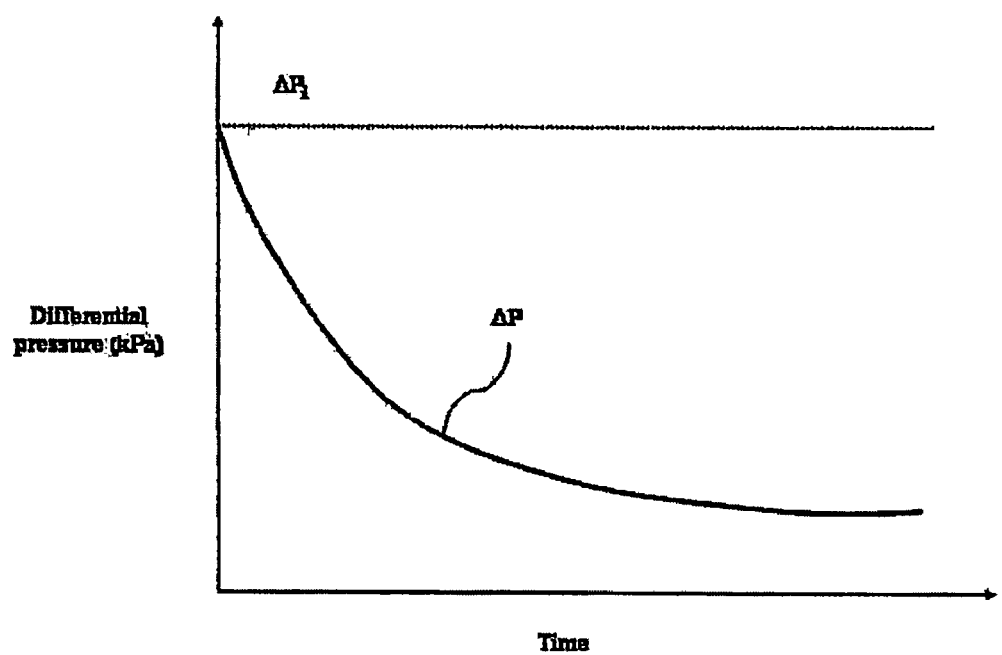
FIG. 6 is a graphic diagram illustrating a differential pressure variation with time by measuring the blood cell deformability according to the present invention.

As shown in FIG. 6, an example of a graphic diagram is presented to illustrate a differential pressure variation with time for measuring the blood cell deformability.

A differential pressure generator (33) is connected to the tiny waste blood pot (23) of the disposable blood sample test kit (20) for continuously generating the vacuum pressure. Therefore, the blood sample is able to flow continuously toward the tiny waste blood pot (23) through the slit channel (22).

As the blood test progresses, the pressure of the tiny waste blood pot (23) is gradually increased from the initial vacuum pressure to the atmospheric pressure according to the increasing volume of the flow of the blood sample. When the vacuum pressure of the tiny waste blood pot (23) approaches the atmospheric pressure, the differential pressure is decreasing as an exponential function to the time variation and finally reaches the balanced atmospheric pressure to terminate the blood test.

If the viscosity of the blood sample and the differential pressure were set constant, the graph of the pressure-time curve would be identical for each blood test. Accordingly, a specific pressure as a function of time could be anticipated without measuring a particular pressure.

Figure 7:
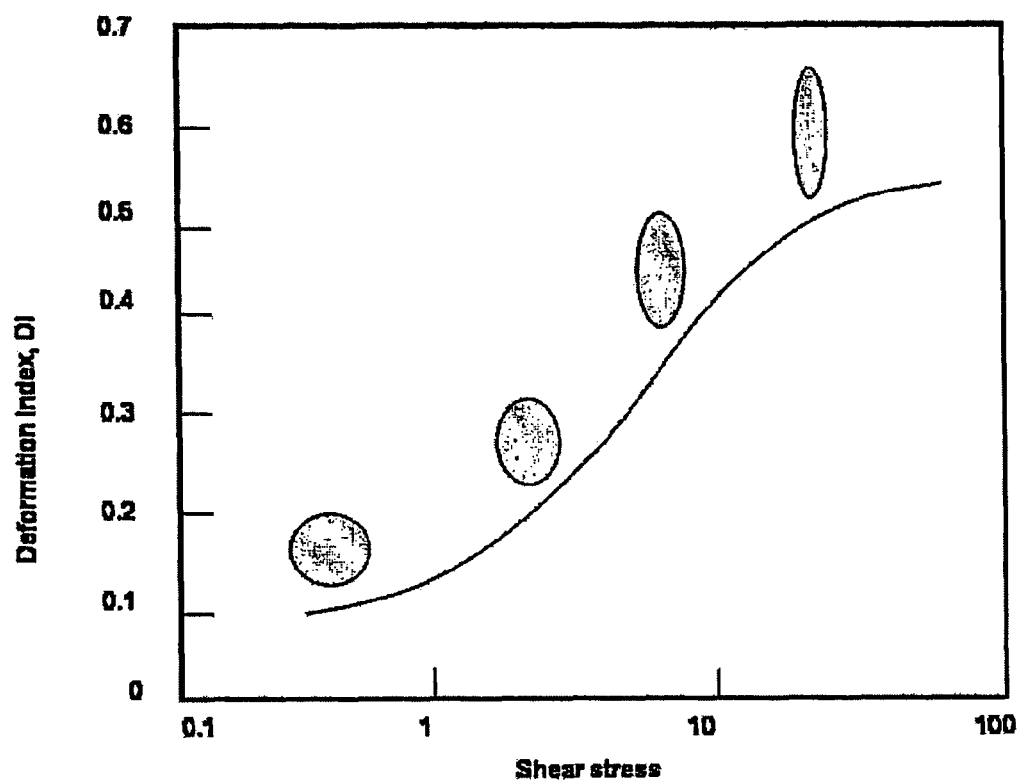
FIG. 7 is a graphic diagram plotted on the Shear Stress variation Deformation Index (DI) coordinate to illustrate the measured blood cell deformability according to the present invention.

As shown in FIG. 7, a graphic diagram of the blood cell deformability plotted on the Wall Shear Stress—Deformation Index (DI) Coordinate is presented. A plurality of images of the deformed blood cells that flow through the slit channel under the various negative pressure conditions is taken to analyze the deformability through the computer program and plotted on the Wall Shear Stress—Deformation. Index (DI) Coordinate.

The Deformation Index (DI) represents the diffracted blood cell images in the ratio of length to breadth and defined in Equation 1 as follows:

$$(L-W)/(L+W), \qquad \text{Equation 1}$$

wherein DI represents Deformation Index, L is the length and W is the width.

If the shear force is small, the Deformation Index (DI) is near zero (0), i.e. the blood cell has a circular shape. As the shear force is increased, the value of Deformation Index (DI) is increased.

Hereinafter, an operating principle and manual of the instrument for measuring a blood cell deformability is described as follows:

First, a droplet of the blood sample is dropped in the tiny blood sample pot (21). At this point, the blood sample is penetrated to the halfway point of the slit channel (22) due to the capillary effect.

Next, the differential pressure generator (33) actuates to generate the differential pressure between the tiny blood sample pot (21) and tiny waste blood pot (23).That is, a vacuum pressure is generated at the tiny waste blood pot (23). The differential pressure generator (33) is connected to the tiny waste blood pot (23) through a connecting tube and valve (32) to generate a vacuum pressure at the tiny waste blood pot (23). A pressure gauge (34) is also connected to the differential pressure generator (33) and to the disposable blood sample test kit (20) for continuously measuring the differential pressures.

Due to the different pressures, i.e. vacuum pressure at the tiny waste blood pot (23) and atmospheric pressure at the tiny blood sample pot (21), the blood sample continuously moves from the tiny blood sample pot (21) to the tiny waste blood pot (23) through the slit channel (22).

As the blood test progresses, the vacuum pressure in the tiny waste blood pot (23) is gradually increased to the atmospheric pressure according to the increasing volume of the flow of the blood sample. Accordingly, as the testing time elapses the pressure difference between the tiny blood sample pot (21) and tiny waste blood pot (23) is diminished, it approaches the balanced atmospheric pressure as an exponential function of time variation and finally terminates the blood test.

The pressure gauge (34) detects the pressure difference ($\Delta P$) between the tiny blood sample pot (21) and tiny waste blood pot (23). Applying the known shear formula with the pressure difference ($\Delta P$), the shear force and shear rate can be calculated by using Equation 2 as shown below: That is, the ideal gas state equation is applied to the volume of the tiny waste blood pot (23), and the instant internal volume (V) can be calculated to each time period.

$$P_{wi} V_{wi} = P_w(t) V_w(t) \qquad \text{Equation 2}$$

Wherein, the sub-letter i represents initial value, and w represents waste blood pot.

As the blood sample flows to the tiny waste blood pot (23) through the slit channel (22), the pressure $P_w(t)$ of the tiny waste blood pot (23) is gradually increased as the time elapses. Therefore, the air volume $V_w(t)$ of the tiny waste blood pot (23) is gradually decreased. The pressure $P_w(t)$ of the tiny waste blood pot (23) is detected by the pressure gauge (34). Therefore, the air volume $V_w(t)$ of the tiny waste blood pot (23) could be calculated by Equation 2.

At this point, the decrement of the air volume $V_w(t)$ in the tiny waste blood pot (23) is the same as the increment of the flow in volume of the blood sample.

$$\Delta V_{w,air} = \Delta V_{liq} \qquad \text{Equation 3}$$

Further, if the volume variation of the blood sample is differentiated based on the time variation, the volume flow rate of the blood sample through the capillary can be found.

$$Q = [\Delta V_{liq}/\Delta t] \qquad \text{Equation 4}$$

The slit channel (22) having a rectangular shape of height H, width W, and length L is loaded with the operating pressures and fluid volume on both ends, and the shear rate could be calculated with the pre-calculated data of the volume variation from Equation 5 as follows:

$$\gamma = (1/3)[6Q/(WH2)][2 + \{d(\ln Q)/d(\ln \tau)\}] \qquad \text{Equation 5:}$$

Further, the shear stress could be calculated from Equation 6 as follows:

$$\tau = [\Delta P(t)H/L]/[(1+2H/W)] \qquad \text{Equation 6}$$

Wherein, $\tau$ represents the shear stress.

It is also possible to apply a different method to calculate the shear force instead of the direct measuring pressure. When the blood sample is prepared, the Buffer solution is dissolved to dilute five micro-liters of blood sample with the mixing rate of 100:1 or 200:1.

Because the volume of the blood sample is very small in the buffer solution, the effect of viscosity of the blood in the diluted blood sample may be ignored. Therefore, the viscosity of the diluted blood sample is considered the same as that of the buffer solution. Even though a different blood sample is diluted into the buffer solution, the viscosity of the diluted blood sample is negligibly changed.

Even though a pressure gauge is used in this invention for detecting the pressure difference, it is possible to calculate the pressure variation with time, if the viscosity of the diluted blood sample, blood flowing resistance, and vacuum pressures were utilized.

Alternatively, an arbitrary blood sample test is performed under the consistent preset conditions. Then, the result of the arbitrary blood sample test can be applied to the specific blood sample test performed under the same consistent preset conditions. Through this means, the shear force can be calculated by applying the pressure variation with time based on the result of the arbitrary blood sample test.

As an implementing example, it is a special character of the present invention that the shear stress can be obtained by the pre-measured data or pre-calculated data of the differential pressure without detecting the instant pressure. It is also possible to plot the graph of the blood cell deformability with respect to the shear force as a function of the time based on the pre-calculated shear stress.

During the differential driving pressure being activated, the blood cells flowing through the slit channel (22) are deformed by the shear force. The light-emitting unit (10) such as a Laser Diode illuminates the deformed blood cells. The emitted light on the deformed blood cell is diffracted, transmitted, and projected on the screen (31) via the slit channel (22) made of a transparent material.

The projected image has an integrated shape of the diffraction-interference image formed by the plural blood cells, which is known as a Laser-Diffraction Technique in the optical art. At this point, the image-capturing unit (35) captures the deformed blood cell image, and a memory unit (38) stores the calculated information and images.

Then, the measured pressure is converted to the shear stress and shear rate through the mathematical formula and the image analysis computer program. Next, the control unit (36) calculates the Deformation Index (DI) and length-breadth ratio for analyzing the blood cell deformability through the image analysis computer programming, such as a curve-fitting program, and plots the graph or chart for the deformed blood cell.

Further, it is necessary to control the blood sample testing temperature because the blood cell deformability is affected by the temperature. The disposable blood test kit (20) must be stored at a consistent temperature to maintain the best conditions for minimizing the heat expansion. The instrument of the present invention adopts a heat control device such as a thermo-electric component in the disposable blood test kit (20). A temperature control block or water jacket may be used for controlling the temperature. A halogen-lamp would be used to preheat the area surrounding the disposable blood test kit (20).

As discussed above and referred to in FIG. 2, the disposable blood test kit (20) is integrally formed with a tiny blood sample pot (21), a slit channel (22), and a tiny waste blood pot (23). Especially, it is designed to be used only as a one-time test and disposed for avoiding the washing process during the blood test.

The disposable blood test kit (20) is usually made of a transparent material such as a Lucite or clear plastic and designed to use a tiny amount of blood sample. Since the disposable blood test kit (20) is manufactured by the precise extrusion, it is possible to be produced by mass-production. Due to the disposable kit, it is safe from virus contamination. It is convenient to use in the private clinic or the general hospital laboratories due to the inexpensive production cost.

The light-emitting unit must adopt a light source that creates the wavelength range of 350 nm ~690 nm, which is diffracted to the blood cells. The light-emitting unit (10) of the present invention equips a Laser Diode with wavelength of 650 nm.

After diffracting to the blood cell, the image of the deformed blood cells is projected on the screen. Then, the image-capturing unit (35) enables capturing the projected images of the deformed blood cells. The image-capturing unit (35) could use a CCD sensor array, CCD camera, web camera, or video camera. However, the CCD camera is adopted in this invention. Alternatively, the image-capturing unit (35) enables directly capturing the deformed blood cell images without projecting the images on the screen.

Figure 8:
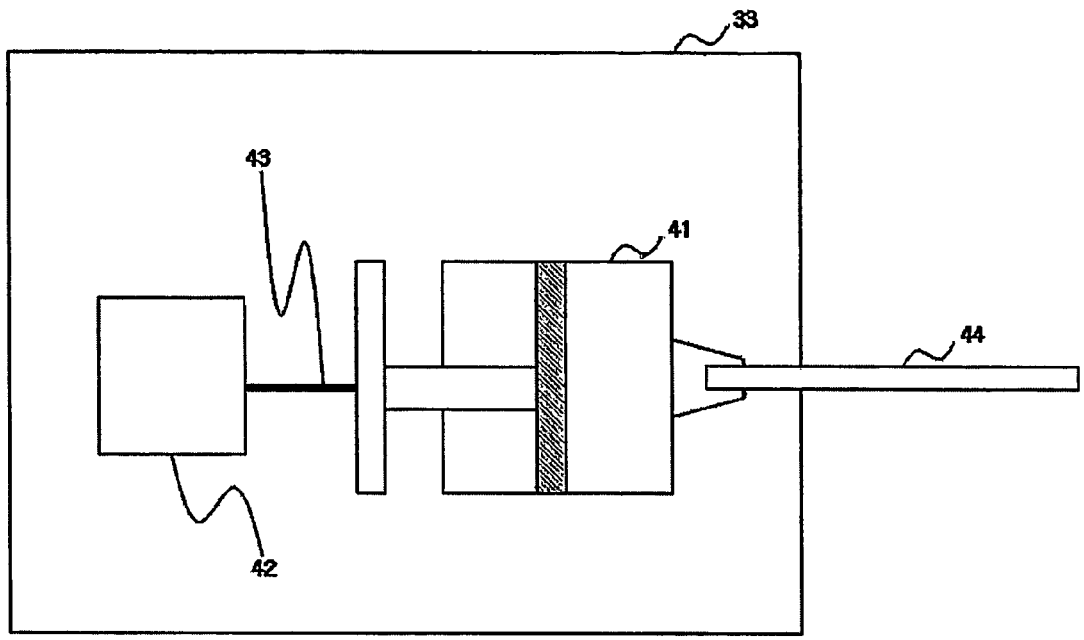
FIG. 8 is an outer configuration of an instrument equipped with a differential pressure generator for measuring the blood cell deformability according to the present invention.

As shown in FIG. 8, an outer configuration of a differential pressure generator is presented as an example.

The differential pressure generator (33) consists of a step motor (42) controlled by the controller (36), a linear movement guide (43), and a syringe (41) forming a piston and cylinder. The differential pressure generator (33) is connected to the vale (32) through the connecting tube (44).

The stroke of the linear movement guide (43) connected to the step motor (42) and syringe (41) is adjustable by moving the rod forward or back, so that the vacuum pressure can be adjusted.

Figure 9:
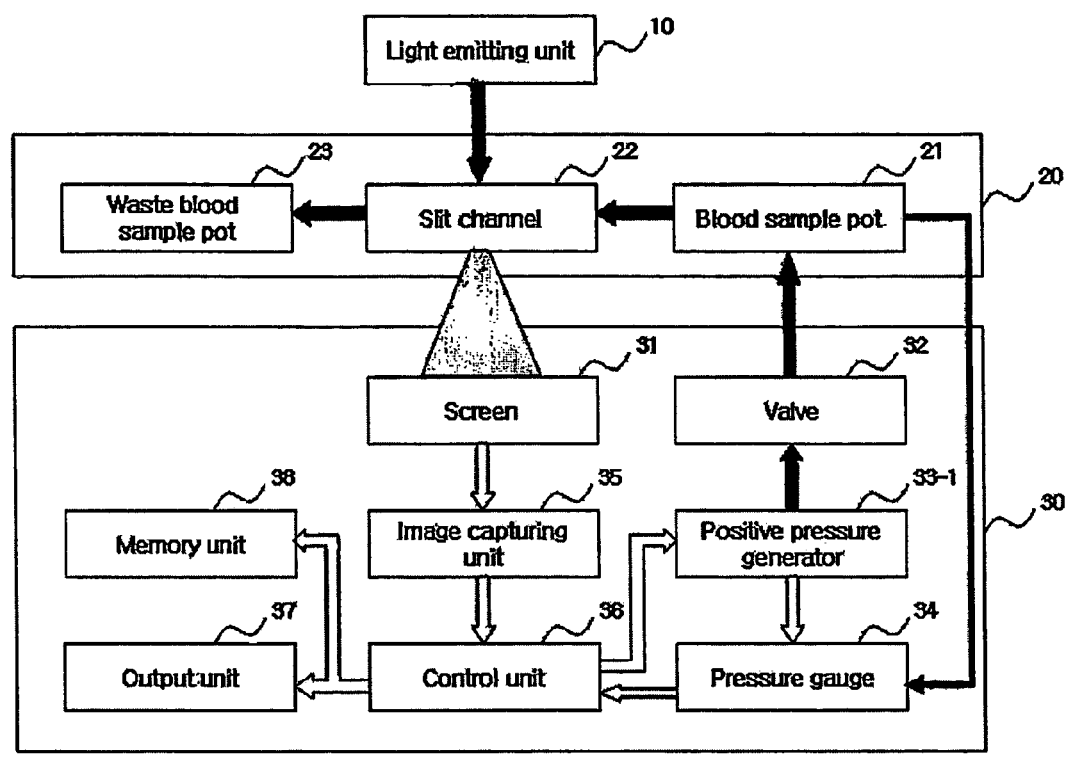
FIG. 9 is a configuration of an instrument equipped with a positive pressure generator for measuring the blood cell deformability according to the second embodiment of the present invention.
Figure 10:
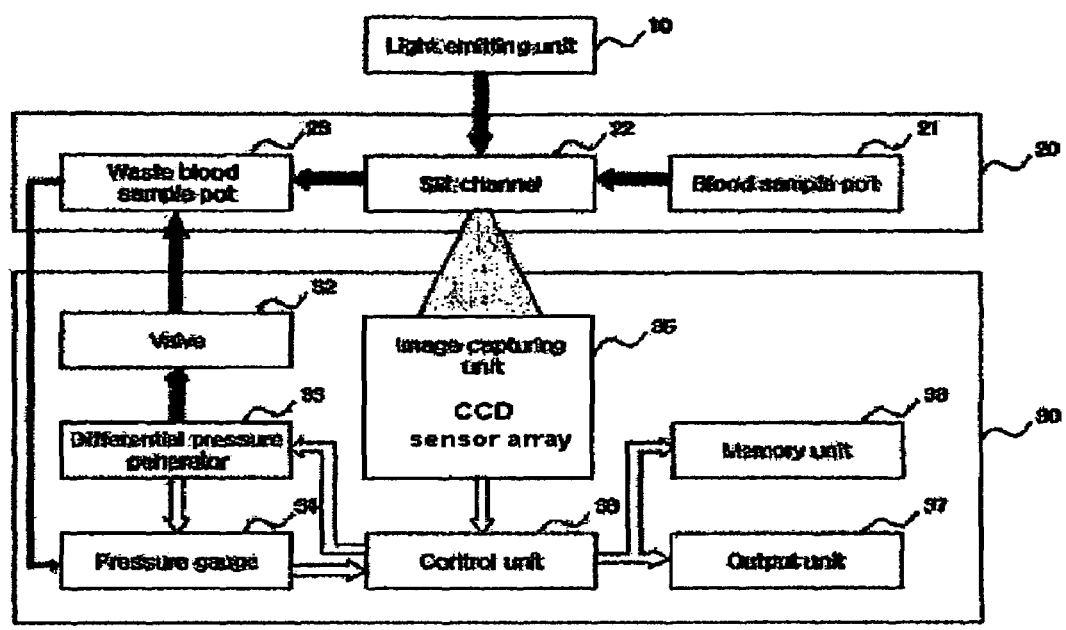
FIG. 10 is an alternative configuration of the instrument equipped with the image capturing unit (35), such as a CCD sensor array for directly capturing the diffracted images without screen of the present invention.

As shown in FIG. 9, a configuration of positive pressure generator adapted to the instrument for measuring the blood cell deformability is presented.

Unlike the vacuum pressure operating system as discussed in FIGS. 1 to 7, the positive pressure operating system adopts a positive pressure generator (33-1) connected to the tiny blood sample pot (21) through the valve (32) and the connecting tube.

Referring to FIG. 9, a configuration of positive pressure operating instrument for measuring the blood cell deformability of the second embodiment comprises a light emitting unit (10) for emitting the light beam to the blood sample, a disposable blood test kit (20) for containing the blood sample, and a measurement unit (30) for measuring the blood cell deformability.

The disposable blood test kit (20) consists of a tiny blood sample pot (21) for containing a droplet of the blood sample, a slit channel (22) for penetrating the blood sample by the positive pressure difference, and a tiny waste blood pot (23) for collecting the tested blood sample. The base of the tiny blood sample pot (21) is connected to one end of the slit channel (22) for supplying the blood sample. The base of the tiny waste blood pot (23) is connected to the opposite end of the slit channel (22) for collecting the tested blood sample.

The measurement unit (30) comprises: a positive pressure generator (33-1) connected to the tiny blood sample pot (21) through a connecting tube and valve (32); a pressure gauge (34) connected to the positive pressure generator (33-1) and the blood sample pot (20) for continuously measuring the positive pressures; a screen (31) for projecting the diffracted images of the blood cell, which is passed through the slit channel (22); an image capturing unit (35) for capturing the blood cell images; a control unit (36) for calculating the blood cell deformability, variation of the shearing force, and deformation on time based on the data received from the pressure gauge (34) and the image capturing unit (35); an output unit (37) for printing the calculated information on the sheet or displaying on an LCD screen; and a memory unit (38) for storing the calculated information and images.

At this point, the positive pressure generator (33-1) produces the positive pressure at the tiny blood sample pot (21), so that the blood sample is enabled to flow forcibly toward the tiny waste blood pot (23) through the slit channel (22). Except for the connecting position, the pressure generator (33-1) has the same configuration as discussed in FIG. 8, and comprises a step motor (42) controlled by the controller (36), a linear movement guide (43), and a syringe (41) forming a piston and cylinder. The operational function and manual are also identical to the previous vacuum pressure system excluding the opposite operating direction for providing the positive pressure on the tiny blood sample pot (21).

Referring to FIG. 6 again, due to the positive pressure loaded to the tiny blood sample pot (21), the blood sample is able to flow continuously toward the tiny waste blood pot (23) through the slit channel (22). As the blood test progresses, the pressure of the tiny blood sample pot (21) is gradually decreased from the initial positive pressure to the atmospheric pressure according to the decreasing volume of the flow of the blood sample. When the positive pressure of the tiny blood sample pot (21) approaches the atmospheric pressure, the pressure is decreasing as an exponential function to the time variation and finally reaches the balanced atmospheric pressure to terminate the blood test.

According to the present invention, it has an excellent effect and merit to obtain the blood cell deformability by utilizing a small amount of blood sample within a short testing time.

It has merit to be conveniently used in the clinic or the general hospital laboratories due to the inexpensive production cost, and its' disposability.

It also has an excellent effect to measure the deformability of the blood cell based on the shear stress by loading the differential pressure.

While this invention has been described in connection with what is presently considered to be the most practical and preferred embodiment, it is to be understood that the invention is not limited to the disclosed embodiment and the drawings, but, on the contrary, it is intended to cover various modifications and variations within the spirit and scope of the appended claims.

What is claimed is:

1. An instrument for measuring blood cell deformability comprising:
    a disposable blood test kit (20) for directly containing the blood sample,
    a light emitting unit (10) disposed above said disposable blood test kit (20),
    a measurement unit (30) for measuring the blood cell deformability,
    said disposable blood test kit (20) comprises a blood sample pot (21) for containing the blood sample, a slit channel (22) for flowing the blood sample by a pressure difference, and a waste blood pot (23) for collecting the tested blood sample, said measurement unit (30) comprises a differential pressure generator (33), which is connected to the disposable blood test kit (20) through a connecting tube and a valve (32) for generating the pressure difference between the blood sample pot (21) and waste blood pot (23), a pressure gauge (34) connected to the differential pressure generator (33) and the disposable blood test kit (20) for measuring the pressure difference, a means for projecting the diffracted images of the blood cell, an image capturing unit (35) for capturing the diffracted images, a control unit (36) for calculating the blood cell deformability and variation of the shearing force according to the blood cell deformation on time based data received from the pressure gauge (34) and the image capturing unit (35), an output unit (37) for printing the calculated information on the sheet or displaying on an LCD screen, and a memory unit (38) for storing the calculated information and images, wherein said control unit (36) further calculates a shearing stress($\pi$) as a function of time, which is calculated and stored by a computer analyses based on time data of pressure measurements, alternatively, said shearing stress ($\pi$) can be determined according to pre-calculated data of pressure without applying the instantly measured pressure data, and the diffracted images of the blood cells captured by the image-capturing unit (35) are analyzed by ellipse curve-fitting computer software to determined a length (L) and a width (W) of analyzed elliptic images, and calculated a Deformation Index (DI) for determining the blood cell deformability and the shearing stress ($\pi$) as a function of time.

2. An instrument for measuring blood cell deformability as claimed in claim 1, wherein said differential pressure generator (33) is connected to the waste blood pot (23) of the disposable blood test kit (20) through a connecting tube and a valve (32) for generating vacuum pressure, negative pressure, at the waste blood pot (23), so that the blood sample flows toward the waste blood pot (23) through the slit channel (22).

3. An instrument for measuring blood cell deformability as claimed in claim 1, wherein said differential pressure generator (33-1) is connected to the blood sample pot (21) of the disposable blood test kit (20) through a connecting tube and a valve (32) for generating positive pressure at the blood sample pot (21), so that the blood sample flows toward the waste blood pot (23) through the slit channel (22).

4. An instrument for measuring blood cell deformability as claimed in claim 1, wherein said slit channel (22) is optically transparent and has a clearance with a rectangular shape.

5. An instrument for measuring blood cell deformability as claimed in claim 1, wherein said disposable blood test kit (20) is made of a transparent material, which is one of silicon, silica, quartz, glass, polymer produced by a laser, an extruded polymer or ceramics.

6. An instrument for measuring blood cell deformability as claimed in claim 1, further comprises a heat control device, which is a thermo-electric component, a temperature control block, a hot-cold water jacket, or a halogen-lamp for adjusting and maintaining constant testing temperature surrounding the disposable blood test kit.

7. An instrument for measuring blood cell deformability as claimed in claim 1, wherein said image capturing unit (35) enables capturing the diffracted images of the deformed blood cell projected on a screen.

8. An instrument for measuring blood cell deformability as claimed in claim 1, wherein said image capturing unit (35) enables directly capturing the diffracted images of the deformed blood cell by employing a CCD sensor array without projecting on a screen.

9. An instrument for measuring blood cell deformability as claimed in claim 1, wherein said image capturing unit (35) can be adopted either a CCD sensor array, CCD camera, digital camera, web camera or video camera for capturing images.

10. An instrument for measuring blood cell deformability as claimed in claim 1, wherein said light-emitting unit (10) is adopted as either a Laser Diode or Light Emitting Diode (LED).

* * * * *